(12) United States Patent
Glaser et al.

(10) Patent No.: US 8,971,602 B2
(45) Date of Patent: Mar. 3, 2015

(54) METHOD FOR MAGNETIC RESONANCE ELASTOGRAPHY USING TRANSIENT WAVEFORMS

(75) Inventors: Kevin J Glaser, Rochester, MN (US); Richard L Ehman, Rochester, MN (US); David A Olsen, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 320 days.

(21) Appl. No.: 13/453,646

(22) Filed: Apr. 23, 2012

(65) Prior Publication Data

US 2012/0269415 A1 Oct. 25, 2012

Related U.S. Application Data

(60) Provisional application No. 61/478,129, filed on Apr. 22, 2011.

(51) Int. Cl.
| | | |
|---|---|---|
| *G06K 9/00* | (2006.01) | |
| *G01R 33/563* | (2006.01) | |
| *A61B 5/055* | (2006.01) | |
| *A61B 5/00* | (2006.01) | |

(52) U.S. Cl.
CPC .......... *G01R 33/56358* (2013.01); *A61B 5/055* (2013.01); *A61B 5/4244* (2013.01); *A61B 5/7292* (2013.01)
USPC .......................................... 382/131; 600/410

(58) Field of Classification Search
CPC .... A61B 5/055; A61B 5/4244; A61B 5/7292; G01R 33/56358
USPC .......................................................... 382/131
See application file for complete search history.

(56) References Cited

U.S. PATENT DOCUMENTS

| | | | |
|---|---|---|---|
| 6,798,192 B2 * | 9/2004 | Faymon et al. ............... | 324/166 |
| 7,257,244 B2 * | 8/2007 | Miga ............................. | 382/128 |
| 7,439,736 B2 * | 10/2008 | Meaney et al. ............... | 324/307 |
| 8,010,176 B2 * | 8/2011 | Sun et al. ...................... | 600/407 |
| 8,094,911 B2 * | 1/2012 | Lindop et al. ................. | 382/131 |
| 8,207,733 B2 * | 6/2012 | Meaney et al. ............... | 324/306 |
| 8,222,901 B2 * | 7/2012 | Chopra et al. ................ | 324/309 |
| 8,508,229 B2 * | 8/2013 | Ehman et al. ................. | 324/318 |
| 2003/0048867 A1 * | 3/2003 | Acharya et al. ................. | 378/18 |
| 2003/0065267 A1 * | 4/2003 | Smith ........................... | 600/466 |
| 2004/0049106 A1 * | 3/2004 | Kanazawa .................... | 600/410 |
| 2004/0234113 A1 * | 11/2004 | Miga ............................. | 382/128 |
| 2005/0054930 A1 * | 3/2005 | Rickets et al. ............... | 600/453 |
| 2005/0270029 A1 * | 12/2005 | Ehman et al. ................. | 324/318 |

(Continued)

OTHER PUBLICATIONS

Bensamoun et al. "Determination of Thigh Muscle Stiffness Using Magnetic Resonance Elastography" Journal of Magnetic Resonance Imaging 23: pp. 242-247 (Dec. 5, 2005).*

(Continued)

*Primary Examiner* — Chan Park
*Assistant Examiner* — Mia M Thomas
(74) *Attorney, Agent, or Firm* — Quarles & Brady, LLP

(57) ABSTRACT

A dynamic magnetic resonance elastography ("MRE") method for quantifying liver stiffness using intrinsic transient waveforms imparted on the liver by the beating heart is provided. The method includes synchronizing motion-encoding gradients in an MRE pulse sequence to the subject's cardiac cycle.

15 Claims, 3 Drawing Sheets

(56) References Cited

U.S. PATENT DOCUMENTS

| | | | |
|---|---|---|---|
| 2006/0012367 A1* | 1/2006 | Meaney et al. | 324/315 |
| 2006/0264736 A1* | 11/2006 | Ehman et al. | 600/410 |
| 2007/0049824 A1* | 3/2007 | Konofagou et al. | 600/437 |
| 2008/0255444 A1* | 10/2008 | Li | 600/411 |
| 2008/0285819 A1* | 11/2008 | Konofagou et al. | 382/128 |
| 2009/0036766 A1* | 2/2009 | Meaney et al. | 600/410 |
| 2010/0045289 A1* | 2/2010 | Chopra et al. | 324/307 |
| 2010/0241012 A1* | 9/2010 | Yin et al. | 600/485 |
| 2011/0025333 A1* | 2/2011 | Ehman et al. | 324/318 |
| 2011/0028828 A1* | 2/2011 | Daye et al. | 600/410 |
| 2011/0160586 A1* | 6/2011 | Li et al. | 600/443 |
| 2012/0053450 A1* | 3/2012 | Salcudean et al. | 600/421 |
| 2012/0269415 A1* | 10/2012 | Glaser et al. | 382/131 |
| 2013/0004044 A1* | 1/2013 | Ross et al. | 382/131 |
| 2013/0197401 A1* | 8/2013 | Sato et al. | 601/2 |
| 2014/0107467 A1* | 4/2014 | Felmlee et al. | 600/411 |
| 2014/0232395 A1* | 8/2014 | Sutton et al. | 324/309 |

OTHER PUBLICATIONS

Georges et al. "Increased Stiffness of the Rat Liver Precedes Matrix Deposition: Implications for Fibrosis" AMJ Physiol Gatrointest Liver Physiol 293: G1147-G1154 (Oct. 11, 2007).*

Rao et al. "Spatial Angular Compounding for Elastography w/o the Incompressibility Assumption" Department of Medical Physics, The University of Wisconsin-Madison, 1300 University Avenue, 1530 MSC, Madison, WI (2005).*

Bae, et al., Ultrasound Thyroid Elastography Using Carotid Artery Pulsation, J. Ultrasound Med., 2007, 26:797-805.

Chung, et al., Liver Stiffness Assessment by Tagged MRI of Cardiac-Induced Liver Motion, Magnetic Resonance in Medicine, 2011, 65:949-955.

Dighe, et al., Differential Diagnosis of Thyroid Nodules with US Elastography Using Carotid Artery Pulsation, Radiology, 2008, 248(2):662-669.

Kanai, Viscoelasticity Measurement of Heart Wall in In Vivo, IEEE Ultrasonics Symposium, 2004, pp. 482-485.

Mai, et al., Strain Imaging of Internal Deformation, Ultrasound in Medicine and Biology, 2002, 28(11/12):1475-1484.

Mariappan, et al., Magnetic Resonance Elastography: A Review, Clinical Anatomy, 2010, 23:497-511.

McCracken, et al., Mechanical Transient-Based Magnetic Resonance Elastography, Magnetic Resonance in Medicine, 2005, 53:628-639.

Neumann, et al., A Novel Approach to Assess the Stiffness of Vessels by Means of Pulse Wave Analysis in Transcutaneous Ultrasound, IEEE Ultrasonics Symposium, 2007, pp. 577-580.

Olsen, et al., Cardiac-Gated Hepatic MR Elastography with Intrinsic Transient Waveforms, Proc. Intl. Soc. Mag. Reson. Med., 2011, #1838.

Pattison, et al., Poroelastic MRE Reconstructions of Brain Acquired with Intrinsic Activation, Proc. Intl. Soc. Mag. Reson. Med., 2010, #3404.

Watanabe, et al., MR Elastography of the Liver at 3 T with Cine-Tagging and Bending Energy Analysis: Preliminary Results, European Radiology, 2010, 20:2381-2389.

Yin, et al., Assessment of Hepatic Fibrosis With Magnetic Resonance Elastography, Clinical Gastroenterology and Hepatology, 2007, 5:1207-1213.

Zhao, et al., Auto-Elastography of the Brain, Proc. Intl. Soc. Mag. Reson. Med., 2009, 17:713.

* cited by examiner

METHOD FOR MAGNETIC RESONANCE ELASTOGRAPHY USING TRANSIENT WAVEFORMS

CROSS-REFERENCE TO RELATED APPLICATIONS

This application claims the benefit of U.S. Provisional Patent Application Ser. No. 61/478,129 filed on Apr. 22, 2011, and entitled "METHOD FOR MAGNETIC RESONANCE ELASTOGRAPHY USING TRANSIENT WAVEFORMS."

STATEMENT REGARDING FEDERALLY SPONSORED RESEARCH

This invention was made with government support under EB001981 and RR018898 awarded by the National Institutes of Health. The government has certain rights in the invention.

BACKGROUND OF THE INVENTION

The field of the invention is systems and methods for magnetic resonance imaging ("MRI"). More particularly, the invention relates to systems and methods for magnetic resonance elastography ("MRE").

Non-alcoholic fatty liver disease ("NAFLD") is a spectrum of liver diseases that represent the most common cause of chronic liver disease in the United States, most likely affecting up to thirty percent of the adult U.S. population. NAFLD can exist as simple steatosis, steatosis with inflammation, and non-alcoholic steatohepatitis ("NASH"). Of these three conditions, NASH involves actual hepatocyte injury and has the potential to progress to cirrhosis in 10-20 percent of cases. Because NAFLD is strongly associated with obesity, there is also concern that the number of cases of NAFLD, and therefore NASH, will increase given the epidemic of obesity in the United States. Currently, the gold standard for definitively distinguishing NASH from other forms of liver disease is by way of a liver biopsy: an invasive procedure not without risk. However, there are a number of new non-invasive imaging modalities that show promise in replacing liver biopsy in the screening of patients with NAFLD.

One such non-invasive method is magnetic resonance elastography ("MRE"), which is a dynamic elasticity imaging technique that mimics the centuries-old diagnostic technique of palpation by applying harmonic mechanical waves to tissue and quantitatively assessing the stiffness of tissue by analyzing the pattern of wave propagation using MRI. In effect, MRE provides a technique for "palpation by imaging." That is to say, MRE allows for "palpation" of deep tissues like the liver and benefits from the fact that the elastic moduli of human tissues vary over a wide range, allowing for enhanced contrast in MRE imaging. Prior research in measuring tissue elasticity involved the application of static tissue stress with measurement by either ultrasound or MRI saturation imaging. MRE is different in that it uses propagating waves, rather than static stress, as a probe.

Conventional harmonic MRE makes use of an external motion driver, a special MRI imaging sequence with oscillating motion-sensitizing gradients, and a data inversion algorithm. The external drivers are usually either an electromechanical driver, a piezoelectric stack driver, or an acoustic speaker pneumatic system that create multiple periods of sinusoidal motion at a single frequency in the tissue of interest. The imaging sequence typically uses several periods of mechanical motion and several phase offsets to sample the wave field. A reconstruction algorithm can then be used to quantify the mechanical properties of the tissue. Clinical studies have established harmonic MRE as a possible alternative to biopsy for assessing liver fibrosis.

Techniques for studying the propagation of transient impulses as it relates to material stiffness have been around for many years in various fields, including acoustics, optics, and geophysics. Transient wave analysis has also been attempted in connection with MRE, as described by P. McCracken, et al., in "Mechanical Transient-Based Magnetic Resonance Elastography," *Magnetic Resonance in Medicine*, 2005; 53:628-639. In this method, phase-contrast MRE acquisition was employed, but an external driver was used as the motion source. In addition, this method was implemented for MRE of the brain, not the liver.

A significant amount of work has been done over the years to measure motion in the brain due to intrinsic pulsations of the cerebrospinal fluid ("CSF") and vasculature due to cardiac motion. In recent work, phase-contrast MR imaging of the brain has provided researchers with images of transient wave propagation in the brain that they have been able to use to provide tissue stiffness information, as described by S. Zhao, et al., in "Auto-Elastography of the Brain," *Proceedings of the ISMRM*, 2009; 713; and by A. J. Pattison, et al., in "Poroelastic MRE Reconstructions of Brain Acquired with Intrinsic Activation," *Proceedings of the ISMRM*, 2010; 3404. These methods employed a gradient-echo, phase-contrast, flow imaging sequence. Such a method, while useful for brain imaging, would be inadequate for imaging in the liver where motion from the heart would confound imaging in addition to supplying transient wave propagation useful for MRE.

Recent work has used intrinsic motion from the heart to measure tissue strain within the liver, as described by S. Chung, et al., in "Liver Stiffness Assessment by Tagged MRI of Cardiac-Induced Liver Motion," *Magnetic Resonance in Medicine*, 2011; 65(4):949-955. This method uses images of tagged MR magnitude signal to measure tissue displacement, rather than using phase-contrast imaging techniques. Additionally, in this method, motion of the wave produced by the heart is not tracked, and tissue stiffness is not calculated. Instead, the method measures strain, which is a relative, not quantitative, measure of tissue mechanical properties. A similar MR tagging technique has also been used for measuring liver strain due to respiratory motion, as described by H. Watanabe, et al., in "MR Elastography of the Liver at 3T with Cine-Tagging and Bending Energy Analysis: Preliminary Results," *European Radiology*, 2010; 20(10):2381-2389. In this method, cardiac-induced motion was not measured and, once again, no transient wave propagation analysis was performed to measure stiffness.

Ultrasonic imaging techniques have been used since the 1980s to track liver motion due to cardiac pulsations, though not always to measure tissue stiffness. Ultrasound-based techniques, while faster than MR techniques, are limited to imaging only through acoustic windows of the body, such as through intercostal spaces, and to measuring only one component of motion.

As noted above, hepatic MRE currently requires the use of an external vibration source ("driver" or "actuator") that produces motion outside of the body that propagates into the body and into the liver. The MRI system can then image this wave propagation in the liver and report the tissue stiffness. The required use of an external driver can be limiting because the driver is extra equipment that must be attached to the patient, can be a source of discomfort for some patients, and has decreased efficiency of getting motion into the liver in obese patients. Being able to perform MRE without the use of an external driver would offer certain advantages over the existing methods.

In light of the foregoing methods, it would be advantageous to provide a method for magnetic resonance elastography that does not rely on an external driver to produce motion in the liver and that can rapidly acquire images so as to not be negatively impacted by cardiac motion.

SUMMARY OF THE INVENTION

The present invention overcomes the aforementioned drawbacks by providing a method for estimating mechanical properties of a tissue using a magnetic resonance imaging ("MRI") system. Particularly, the method utilizes the transient wave motion intrinsic to the subject under examination as the source of motion to be imaged by a magnetic resonance elastography ("MRE") procedure. In this manner, an external source of motion is not required.

It is an aspect of the invention to provide a method for estimating mechanical properties of a tissue in a subject using an MRI system. The method includes acquiring positive phase image data with the MRI system by performing a pulse sequence that employs a motion-encoding gradient substantially in-phase with transient wave motion propagating through the tissue. The method further includes acquiring negative phase image data with the MRI system by performing a pulse sequence that employs a motion-encoding gradient substantially out-of-phase with transient wave motion propagating through the tissue. Positive and negative wave images are reconstructed from the acquired positive phase image data and the negative phase image data, respectively, and mechanical properties of the tissue are reconstructed using the positive and negative wave images.

It is another aspect of the invention to provide a method for estimating mechanical properties of a tissue using an MRI system. The method includes acquiring an electrocardiograph ("ECG") signal and selecting a temporal offset with respect to the ECG signal. Positive phase image data is acquired with the MRI system by performing a pulse sequence that employs a motion-encoding gradient substantially in-phase with transient wave motion propagating through the tissue, the motion-encoding gradient being timed to occur at the selected temporal offset. Additionally, negative phase image data is acquired with the MRI system by performing a pulse sequence that employs a motion-encoding gradient substantially out-of-phase with transient wave motion propagating through the tissue, the motion-encoding gradient being timed to occur at the selected temporal offset. Several repetitions of the pulse sequences are performed while selecting a different temporal offset for each repetition in order to acquire a positive phase image data set that includes positive phase image data corresponding to each temporal offset and a negative phase image data set that includes negative phase image data corresponding to each temporal offset. Positive wave images and negative wave images are reconstructed from the acquired positive phase image data set and the negative phase image data set, respectively, and mechanical properties of the tissue are calculated using the reconstructed positive and negative wave images.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

In conventional magnetic resonance elastography ("MRE"), an external vibration source generates harmonic waves that are used to characterize tissue. For example, a passive acoustic driver is used to generate vibratory motion in the tissue of a subject under examination. Although these traditional methods of MRE are reliable, it would be beneficial to provide a method for MRE that does not require an external vibration source to generate tissue motion in the subject.

A method for MRE that does not require an external vibration source is provided. This method utilizes sources of in vivo transient motion that is intrinsic to the subject as the source of tissue motion to be imaged in the MRE procedure. By way of example, the subject's beating heart may be used as a source of transient motion. The transient motion generated by the beating heart is conveyed to the subject's liver and, therefore, may be relied upon as a source of generating transient motion for performing MRE of the liver. In this instance, motion-encoding gradients are synchronized to the patient's cardiac cycle. The motion of the beating heart does not provide a steady-state motion at a fixed frequency in the liver. Rather, the motion of the beating heart is a transient impulse, similar to a shock wave. Phase-contrast MRI techniques may be used to image the motion in connection with wave-tracking analysis, which is used to measure the wave speed in the images.

As noted, because the heart is typically adjacent to the liver, the motion of the beating heart produces an impulsive, transient mechanical wavefront that propagates through the liver. Using a modified MRE acquisition method, this transient motion can be recorded and tracked. Images of the propagation of this wavefront can be analyzed to measure the wave speed of the wavefront, which can in turn be used to measure the tissue stiffness. With this technique, no external MRE driver is required to perform MRE of the subject. Such a technique provides a method that requires less equipment to be attached to the patient, thereby improving patient comfort. This method is also beneficial for those patients whose size would otherwise make the generation of motion in an internal organ by way of an externally position vibration source infeasible.

The provided method differs from traditional MRE in significant ways. First, as noted, rather than using an external motion source, the method uses naturally-occurring transient mechanical waves to impart motion on the tissue-of-interest. Second, the method uses transient waveforms rather than the steady-state waveforms utilized by existing MRE techniques.

Figure 1:
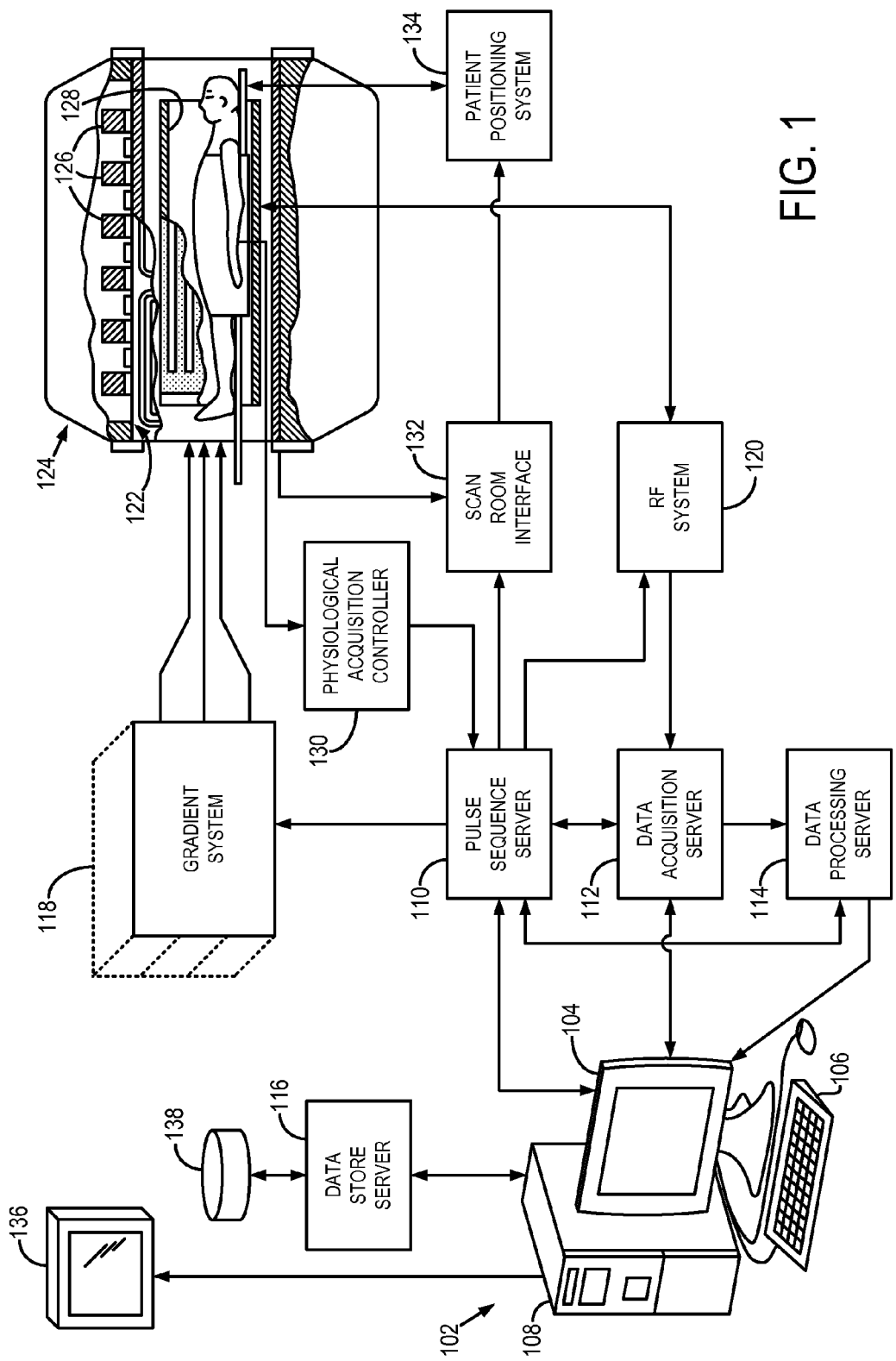
FIG. 1 is a block diagram of an exemplary magnetic resonance imaging ("MRI") system that employs the present invention.

Referring particularly now to FIG. 1, an exemplary magnetic resonance imaging ("MRI") system 100 is illustrated. The MRI system 100 includes a workstation 102 having a display 104 and a keyboard 106. The workstation 102 includes a processor 108, such as a commercially available programmable machine running a commercially available operating system. The workstation 102 provides the operator interface that enables scan prescriptions to be entered into the MRI system 100. The workstation 102 is coupled to four servers: a pulse sequence server 110; a data acquisition server 112; a data processing server 114, and a data store server 116. The workstation 102 and each server 110, 112, 114 and 116 are connected to communicate with each other.

The pulse sequence server 110 functions in response to instructions downloaded from the workstation 102 to operate a gradient system 118 and a radio frequency ("RF") system 120. Gradient waveforms necessary to perform the prescribed scan are produced and applied to the gradient system 118, which excites gradient coils in an assembly 122 to produce the magnetic field gradients $G_x$, $G_y$, and $G_z$ used for position encoding MR signals. The gradient coil assembly 122 forms part of a magnet assembly 124 that includes a polarizing magnet 126 and a whole-body RF coil 128.

RF excitation waveforms are applied to the RF coil 128, or a separate local coil (not shown in FIG. 1), by the RF system 120 to perform the prescribed magnetic resonance pulse sequence. Responsive MR signals detected by the RF coil 128, or a separate local coil (not shown in FIG. 1), are received by the RF system 120, amplified, demodulated, filtered, and digitized under direction of commands produced by the pulse sequence server 110. The RF system 120 includes an RF transmitter for producing a wide variety of RF pulses used in MR pulse sequences. The RF transmitter is responsive to the scan prescription and direction from the pulse sequence server 110 to produce RF pulses of the desired frequency, phase, and pulse amplitude waveform. The generated RF pulses may be applied to the whole body RF coil 128 or to one or more local coils or coil arrays (not shown in FIG. 1).

The RF system 120 also includes one or more RF receiver channels. Each RF receiver channel includes an RF amplifier that amplifies the MR signal received by the coil 128 to which it is connected, and a detector that detects and digitizes the I and Q quadrature components of the received MR signal. The magnitude of the received MR signal may thus be determined at any sampled point by the square root of the sum of the squares of the I and Q components:

$$M=\sqrt{I^2+Q^2} \qquad (1);$$

and the phase of the received MR signal may also be determined:

$$\phi = \tan^{-1}\left(\frac{Q}{I}\right). \qquad (2)$$

The pulse sequence server 110 also optionally receives patient data from a physiological acquisition controller 130. The controller 130 receives signals from a number of different sensors connected to the patient, such as electrocardiograph ("ECG") signals from electrodes, or respiratory signals from a bellows or other respiratory monitoring device. Such signals are typically used by the pulse sequence server 110 to synchronize, or "gate," the performance of the scan with the subject's heart beat or respiration.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized MR signal samples produced by the RF system 120 are received by the data acquisition server 112. The data acquisition server 112 operates in response to instructions downloaded from the workstation 102 to receive the real-time MR data and provide buffer storage, such that no data is lost by data overrun. In some scans, the data acquisition server 112 does little more than pass the acquired MR data to the data processor server 114. However, in scans that require information derived from acquired MR data to control the further performance of the scan, the data acquisition server 112 is programmed to produce such information and convey it to the pulse sequence server 110. For example, during prescans, MR data is acquired and used to calibrate the pulse sequence performed by the pulse sequence server 110. Also, navigator signals may be acquired during a scan and used to adjust the operating parameters of the RF system 120 or the gradient system 118, or to control the view order in which k-space is sampled.

The data processing server 114 receives MR data from the data acquisition server 112 and processes it in accordance with instructions downloaded from the workstation 102. Such processing may include, for example: Fourier transformation of raw k-space MR data to produce two or three-dimensional images; the application of filters to a reconstructed image; the performance of a backprojection image reconstruction of acquired MR data; the generation of functional MR images; and the calculation of motion or flow images.

Images reconstructed by the data processing server 114 are conveyed back to the workstation 102 where they are stored. Real-time images are stored in a data base memory cache (not shown in FIG. 1), from which they may be output to operator display 112 or a display 136 that is located near the magnet assembly 124 for use by attending physicians. Batch mode images or selected real time images are stored in a host database on disc storage 138. When such images have been reconstructed and transferred to storage, the data processing server 114 notifies the data store server 116 on the workstation 102. The workstation 102 may be used by an operator to archive the images, produce films, or send the images via a network to other facilities.

Figure 2:
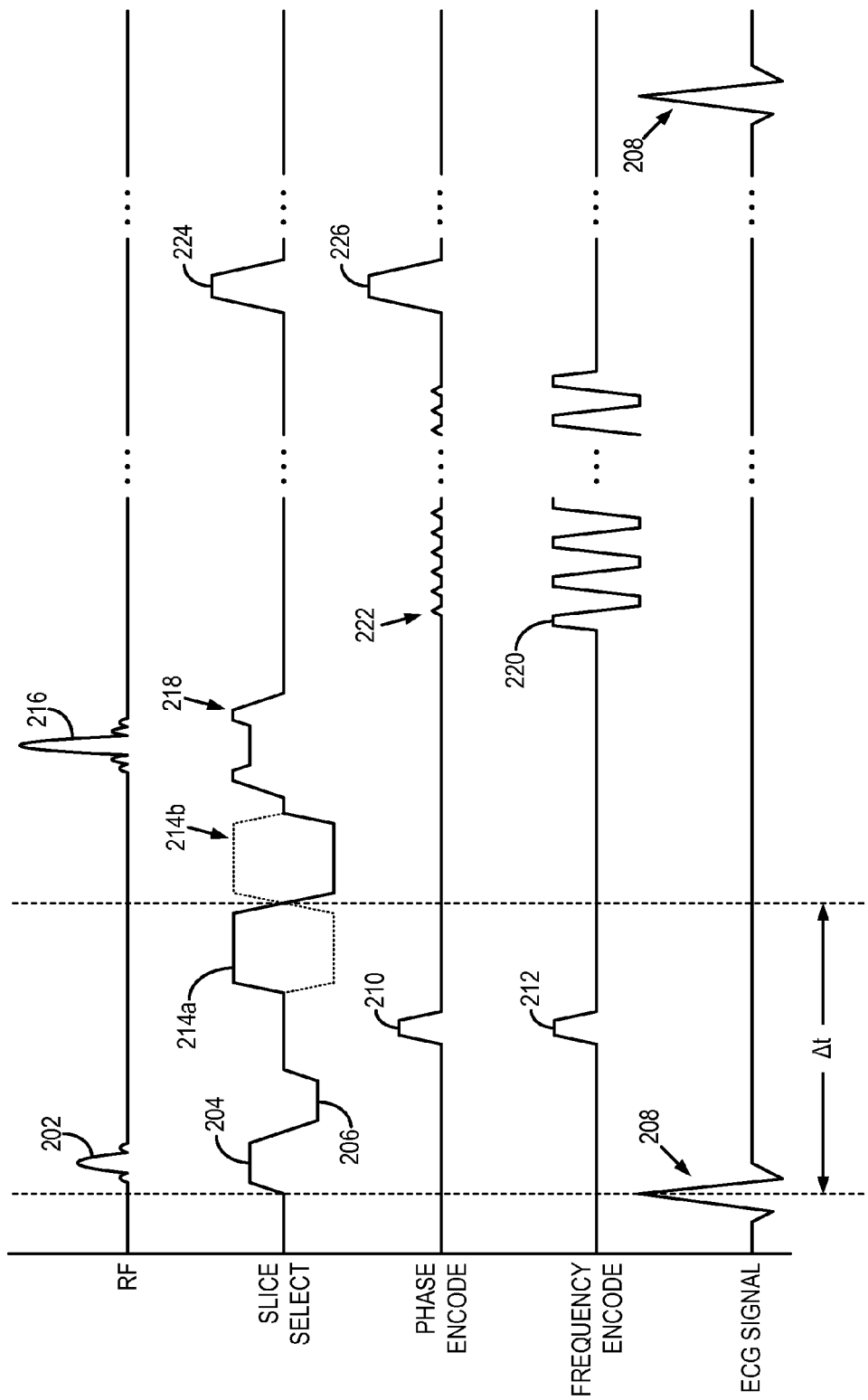
FIG. 2 is a pulse sequence diagram illustrating an exemplary pulse sequence for performing magnetic resonance elastography in accordance with embodiments of the present invention.

Referring particularly to FIG. 2, an example of a pulse sequence that may be used to acquire magnetic resonance image data according to embodiments of the present invention, is shown. The pulse sequence is based on a spin-echo echo-planar imaging ("EPI") sequence. Transverse magnetization is produced by a radio frequency ("RF") excitation pulse 202 that is produced in the presence of a slice-selective gradient 204. To mitigate signal losses resulting from phase dispersions produced by the slice-selective gradient 204, a rephasing lobe 206 is applied after the slice-selective gradient 204. The RF excitation pulse 202 is produced at a preselected time delay following the QRS complex 208 of an ECG signal acquired during the imaging session. The time delay may be selected so that the RF excitation pulse 202 is produced during, immediately after, or some other amount of time after the QRS complex 208. As will be described below, the time delay is implemented to acquire different image data sets with motion encoding for different temporal offsets, $\Delta t$.

Following the application of the slice-selective gradient 204, a prephasing gradient 210 is played out along the phase-encoding direction and another prephasing gradient 212 is played out along the frequency-encoding direction. These prephasing gradients 210, 212, serve to prepare the transverse magnetization for data acquisition by effectively moving the sampling of k-space to a first location in k-space. A motion-encoding gradient 214a is then played out along a motion-encoding direction. For example, as illustrated in FIG. 2, the motion-encoding gradient 214a may be played out along the slice-encoding direction. In the alternative, the motion-encoding gradient 214a may be played out along the phase-encoding direction, the frequency-encoding direction, or some combination of these three directions so as to encode motion in an oblique direction. The spectral characteristics of the motion-encoding gradient 214a are designed based on the spectral characteristics of the motion produced by the heart. By way of example, this frequency of the motion-encoding gradient 214a may be set at 50 Hz.

The phase of the echo signals produced by the pulse sequence is indicative of the movement of the spins during the pulse sequence. If the spins are stationary, the phase of the echo signals is not altered by the motion-encoding gradient 214a, whereas spins moving along the motion-encoding direction will accumulate a phase related to the characteristics of the motion and the motion-encoding gradient 214a. Spins that move in-synchronism and in-phase with the motion-encoding gradient 214a will accumulate maximum phase of one polarity, and those that move in-synchronism, but 180 degrees out-of-phase with the motion-encoding gradient 214a will accumulate maximum phase of the opposite polarity. The phase of the acquired image data is thus affected by the "synchronous" movement of spins along the motion-encoding direction. As illustrated in FIG. 2, the pulse sequence is repeated with the polarity of the motion-encoding gradient 214a is changed, as indicated at 214b, in order to acquire an in-phase image data set and an out-of-phase image data set that can be used to produce phase-difference wave images. By way of example, the motion-encoding gradients 214a, 214b may be timed to occur at the temporal offset, Δt. More particularly, the motion-encoding gradients 214a, 214b may be timed such that they are temporally centered about the temporal offset, Δt.

Next, a rephasing RF pulse 216 is applied in the presence of another slice-selective gradient 218. In order to substantially reduce unwanted phase dispersions, crusher gradients bridge the slice-selective gradient 218. An alternating readout gradient pulse train 220 is then produced in order to form echo signals from which image data is acquired. A spin-echo signal is formed in the middle of the readout pulse train 220 while a gradient-echo signal is acquired during each positive and negative pulse peak of the readout pulse train 220. A phase-encoding gradient "blip" 222 is applied between each readout pulse peak to separately phase encode each acquired gradient-echo signal. Following the conclusion of the readout gradient pulse train 220, a spoiler gradient 224 is played out along the slice-encoding direction and another spoiler gradient 226 is played out along the phase-encoding gradient to prepare the spins for subsequent data acquisitions. The data acquisition is repeated a plurality of times using a different temporal offset, Δt, in each repetition to obtain wave images showing the propagation of the transient waves through the tissue over time (e.g., to track the transient impulses produced by the heart as they propagate through the liver). The data acquisition can also be repeated a plurality of times with a different first slice-selective gradient 204 and second slice-selective gradient 218 applied during each repetition such that multiple slices of image data are acquired.

The physical properties of tissue are measured using MRE by applying a stress and observing the resulting strain. In this method, the stress is intrinsically applied by the beating heart. By measuring the resulting strain, elastic properties of the tissue such as Young's modulus, Poisson's ratio, shear modulus, and bulk modulus can be calculated. Moreover, by measuring the strain in multiple directions, the elastic properties of the tissue can be completely defined.

The attenuation of the strain wave can be estimated by observing the rate at which the strain decreases as a function of distance from the stress producing source. From this, the viscous properties of the gyromagnetic medium may be estimated. The dispersion characteristics of the medium can be estimated by observing the speed and attenuation of the strain waves as a function of their frequency. Dispersion is potentially a very important parameter for characterizing tissues in medical imaging applications.

Typically, a single slice is imaged with motion-encoding performed in three orthogonal directions in three different acquisitions. Imaging in other planes may also be performed, and multi-slice imaging is also possible. The data acquisition may be performed over several breath holds; however, the acquisition may also be respiratory gated so that the subject can breathe freely during the scan.

Figure 3:
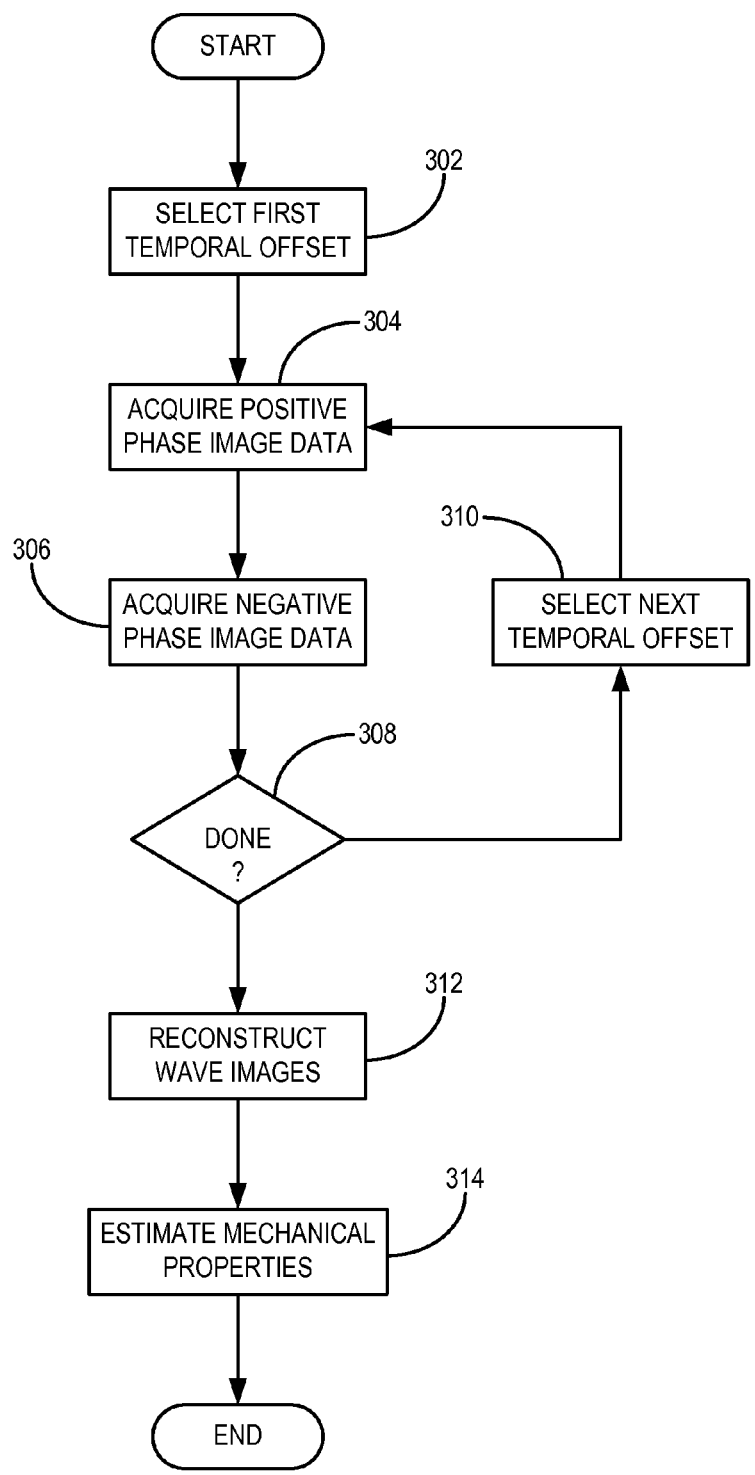
FIG. 3 is a flowchart setting forth the steps of an exemplary method for acquiring image data, reconstructing images, and estimating mechanical properties of a tissue using intrinsic transient waveforms to supply motion to the tissue.

Referring now to FIG. 3, a flowchart setting forth the steps of an example of a method for acquiring image data, reconstructing images, and estimating mechanical properties of a tissue using transient mechanical waves intrinsic in the subject under examination to supply motion to the subject's own tissue is illustrated. The method begins with the selection of a first temporal delay, as indicated at step 302. As described above, this temporal delay may be selected with respect to a portion of an electrocardiograph ("ECG") signal, such as the occurrence of the R-wave in a QRS complex. Positive phase image data is then acquired using a pulse sequence, such as the one in FIG. 2, as indicated at step 304. In this acquisition, the polarity of the motion-encoding gradient is selected to be in-phase with the transient motion. For example, the motion-encoding gradients are synchronized to the patient's cardiac cycle. Following the acquisition of the positive phase image data, negative phase image data is acquired, as indicated at step 306. In this acquisition, the polarity of the motion-encoding gradient is switched, so that the motion-encoding gradient is out-of-phase with the transient motion. A decision is then made at decision block 308 whether the desired amount of image data has been acquired with the desired amount of temporal offsets. If not, then a next temporal offset is selected at step 310. For example, temporal offsets may be selected sequentially such that a plurality of positive and negative phase image data sets are acquired at successively longer times relative to the occurrence of an R-wave.

After all of the desired image data has been acquired, wave images are reconstructed from the positive and negative phase image data sets, as indicated at step 312. The wave images are reconstructed in the usual fashion from the acquired image data. For example, a wave image is reconstructed using a Fourier-based reconstruction technique. The wave images are then used to calculate the mechanical properties of the tissue, as indicated at step 314. The mechanical properties of the tissue are calculated using the wave images in accordance with traditional MRE techniques. For example, the wave images are used to determine the wave speed at each pixel location in the field-of-view covered by the wave images. The wave speed is then used to calculate mechanical properties, such as tissue stiffness.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for estimating mechanical properties of a tissue in a subject using a magnetic resonance imaging (MRI) system, the steps of the method comprising:
    a) acquiring positive phase image data with the MRI system by performing a pulse sequence that employs a motion-encoding gradient substantially in-phase with transient wave motion propagating through the tissue, wherein the transient wave motion is generated by a source intrinsic to the subject;
    b) acquiring negative phase image data with the MRI system by performing a pulse sequence that employs a motion-encoding gradient substantially out-of-phase with transient wave motion propagating through the tissue, wherein the transient wave motion is generated by a source intrinsic to the subject;
    c) reconstructing positive and negative wave images from the acquired positive phase image data and the negative phase image data, respectively; and
    d) calculating mechanical properties of the tissue using the reconstructed positive and negative wave images.

2. The method as recited in claim 1 in which the positive and negative phase image data are acquired using a spin-echo echo-planar imaging pulse sequence.

3. The method as recited in claim 1 in which the transient wave motion includes transient mechanical waves generated by beating of the subject's heart.

4. The method as recited in claim 3 in which steps a) and b) include selecting a frequency of the motion-encoding gradient based on spectral characteristics of the beating of the subject's heart.

5. The method as recited in claim 1 in which step a) includes starting the motion-encoding gradient such that the motion-encoding gradient is temporally in-phase with the subject's cardiac cycle.

6. The method as recited in claim 1 in which step b) includes starting the motion-encoding gradient such that the motion-encoding gradient is temporally out-of-phase with the subject's cardiac cycle.

7. The method as recited in claim 1 further comprising:
    e) acquiring an electrocardiograph (ECG) signal from the subject; and
    f) selecting a temporal offset with respect to the ECG signal.

8. The method as recited in claim 7 in which at least one of steps a) and b) includes performing a pulse sequence in which the motion-encoding gradient occurs at a time relative to the temporal offset selected in step f).

9. The method as recited in claim 8 in which the time relative to the temporal offset is such that the motion-encoding gradient is temporally centered about the temporal offset selected in step f).

10. A method for estimating mechanical properties of a tissue using a magnetic resonance imaging (MRI) system, the steps of the method comprising:
    a) acquiring an electrocardiograph (ECG) signal;
    b) selecting a temporal offset with respect to the ECG signal;
    c) acquiring positive phase image data with the MRI system by performing a pulse sequence that employs a motion-encoding gradient substantially in-phase with transient wave motion propagating through the tissue, the motion-encoding gradient being timed to occur at the temporal offset, wherein the transient wave motion is generated by a source intrinsic to the subject;
    d) acquiring negative phase image data with the MRI system by performing a pulse sequence that employs a motion-encoding gradient substantially out-of-phase with transient wave motion propagating through the tissue, the motion-encoding gradient being timed to occur at the temporal offset, wherein the transient wave motion is generated by a source intrinsic to the subject;
    e) repeating steps c) and d) while selecting a different temporal offset for each repetition in order to acquire a positive phase image data set that includes positive phase image data corresponding to each temporal offset and a negative phase image data set that includes negative phase image data corresponding to each temporal offset;
    f) reconstructing positive wave images and negative wave images from the acquired positive phase image data set and the negative phase image data set, respectively; and
    g) calculating mechanical properties of the tissue using the reconstructed positive and negative wave images.

11. The method as recited in claim 10 in which step g) includes producing wave images using the positive waves images and the negative wave images, the wave images depicting a wavefront of the transient wave motion at each temporal offset.

12. The method as recited in claim 11 in which step g) includes calculating a wave speed from the wave images.

13. The method as recited in claim 10 in which the mechanical properties of the tissue include a stiffness of the tissue.

14. The method as recited in claim 10 in which the tissue is liver tissue.

15. The method as recited in claim 10 in which at least one of steps c) and d) includes performing a pulse sequence in which the motion-encoding gradient is timed to occur at the temporal offset selected in step b) such that the motion-encoding gradient is temporally centered about the temporal offset.

* * * * *